US012369791B2

(12) United States Patent
Longo et al.

(10) Patent No.: US 12,369,791 B2
(45) Date of Patent: Jul. 29, 2025

(54) BINOCULAR REFRACTION INSTRUMENT, SET OF TEST IMAGES, BINOCULAR REFRACTION METHOD AND COMPUTER PROGRAM ASSOCIATED THEREOF

(71) Applicant: Essilor International, Charenton-le-pont (FR)

(72) Inventors: Adéle Longo, Charenton-le-pont (FR); Gildas Marin, Charenton-le-pont (FR); Martha Hernandez-Castaneda, Charenton-le-pont (FR)

(73) Assignee: Essilor International, Charenton-le-Pont (FR)

( * ) Notice: Subject to any disclaimer, the term of this patent is extended or adjusted under 35 U.S.C. 154(b) by 580 days.

(21) Appl. No.: 17/614,477

(22) PCT Filed: May 28, 2020

(86) PCT No.: PCT/EP2020/064902
§ 371 (c)(1),
(2) Date: Nov. 26, 2021

(87) PCT Pub. No.: WO2020/239943
PCT Pub. Date: Dec. 3, 2020

(65) Prior Publication Data
US 2022/0225872 A1 Jul. 21, 2022

(30) Foreign Application Priority Data
May 31, 2019 (EP) ..................................... 19305700

(51) Int. Cl.
A61B 3/02 (2006.01)
A61B 3/00 (2006.01)
(Continued)

(52) U.S. Cl.
CPC ............ *A61B 3/032* (2013.01); *A61B 3/0033* (2013.01); *G06T 7/0012* (2013.01)

(58) Field of Classification Search
CPC ........... A61B 3/103; A61B 3/14; A61B 3/113; A61B 3/125; A61B 3/024; A61B 3/1015;
(Continued)

(56) References Cited

U.S. PATENT DOCUMENTS 6,318,857 B1 * 11/2001 Shirayanagi ........... G02C 7/085
351/158
2006/0087618 A1 * 4/2006 Smart ...................... A61B 3/08
351/209
(Continued)

FOREIGN PATENT DOCUMENTS

CN   105916432 A   8/2016
CN   108351685 A   7/2018
(Continued)

OTHER PUBLICATIONS

Office Action issued Oct. 23, 2023, in corresponding Japanese Patent Application No. 2021-571435 (with English Translation), 6 pages.
(Continued)

*Primary Examiner* — Dawayne Pinkney
(74) *Attorney, Agent, or Firm* — Oblon, McClelland, Maier & Neustadt, L.L.P.

(57) ABSTRACT

The invention concerns a couple of test images, for a binocular refraction method, that comprises: —a first test image (21) to be provided to a first eye of a subject, comprising a central image (21c) surrounded by a first peripheral image (21p), this central image comprising at least one optotype (21o); and—a second test image (22) to be provided to a second eye of the subject, comprising a central image (22c) surrounded by a second peripheral
(Continued)

image (22p) substantially identical to the first peripheral image, this central image being deprived of optotypes, or comprising only optotypes (22o) with a low contrast or sharpness level. The invention concerns also an associated binocular refraction method and refraction instrument, and an associated computer program.

14 Claims, 4 Drawing Sheets

(51) Int. Cl.
*A61B 3/032* (2006.01)
*A61B 3/10* (2006.01)
*G06T 7/00* (2017.01)

(58) Field of Classification Search
CPC ... G02C 5/00; G02C 7/02; G02C 7/04; G02C 7/00; G02B 3/12
USPC ....... 351/241, 239, 200, 205, 206, 210, 219, 351/222, 246, 41, 160 R, 161, 176, 351/159.01, 159.02, 159.34
See application file for complete search history.

(56) References Cited

U.S. PATENT DOCUMENTS

| | | | | |
|---|---|---|---|---|
| 2013/0162784 A1* | 6/2013 | Ueda | ................... | H04N 13/296 348/E5.045 |
| 2014/0002587 A1* | 1/2014 | Aguren | ................. | H04N 5/272 348/46 |
| 2015/0226969 A1* | 8/2015 | Tsukahara | ............... | G06T 19/20 359/462 |
| 2015/0234206 A1* | 8/2015 | Lee | ........................ | G02C 7/083 351/158 |
| 2017/0000331 A1 | 1/2017 | Samec et al. | | |
| 2017/0164822 A1 | 6/2017 | Kalder et al. | | |
| 2017/0340200 A1 | 11/2017 | Blaha et al. | | |

FOREIGN PATENT DOCUMENTS

| | | |
|---|---|---|
| EP | 3 175 776 A1 | 6/2017 |
| JP | 2005-524432 A | 8/2005 |
| JP | 2006-122661 A | 5/2006 |
| JP | 2017-526078 A | 9/2017 |
| JP | 2019-531769 A | 11/2019 |
| KR | 10-2009-0040034 A | 4/2009 |

OTHER PUBLICATIONS

International Search Report and Written Opinion issued on Jul. 30. 2020 in PCT/EP2020/064902 filed on May 28, 2020.

Tyczka, D. R. et al., "Development of a dichoptic foveal/peripheral head-mounted display with partial binocular overlap," Proc. of SPIE, vol. 8041, 2011, pp. 80410F-1-80410F-12.

Alais, D. et al., "Binocular rivalry and perceptual ambiguity," Oxford Handbook of Perceptual Organization, Oxford University Press, 2014, pp. 1-27.

Johnson, C. A. et al., "Effects of Luminance, Contrast, and Blur on Visual Acuity," Optometry and Vision Science, vol. 72, No. 12, 1995, pp. 864-869.

Translation of Chinese Office Action and Search Report issued Apr. 30, 2024 in Chinese Application 202080039783.8, 4 pages.

Office Action dated Sep. 25, 2024, issued in counterpart KR Application No. 10-2021-7037541, with English Translation, (19 pages).

* cited by examiner

BINOCULAR REFRACTION INSTRUMENT, SET OF TEST IMAGES, BINOCULAR REFRACTION METHOD AND COMPUTER PROGRAM ASSOCIATED THEREOF

TECHNICAL FIELD OF THE INVENTION

The invention relates to a binocular refraction instrument configured to display a first test image comprising at least one optotype, to a first eye of a subject, and to display a second test image to a second eye of the subject, the first and second test images being at least partly different from each other. The invention relates also to a binocular refraction method, to a computer program and to a set of test images associated to such a method.

BACKGROUND INFORMATION AND PRIOR ART

In a conventional binocular refraction protocol, the subject has both eyes opened. A test image comprising optotypes is provided to a first eye of the subject and the usual steps of fogging, defogging, fine adjustment of the sphere and astigmatism characterization are carried on for this eye. Meanwhile, a blank image is provided to the second eye of the subject. Then, the test image is provided to the second eye of the subject to determine refraction errors of this second eye, while the blank image is provided to the first eye of the subject.

But some subjects have a binocular vision that is strongly dominated by the image perceived by one of their eyes, called the dominant eye. In other words, such subjects have one visual pathway that dominates strongly over the other visual pathway, in the neural process of binocular image fusion. For such subjects, during the binocular refraction protocol described above, a "suppression" phenomenon may occur when the blank image is provided to the dominant eye of the subject, due to ocular rivalry between the left and right visual pathways of the subject. In this case, the image perceived by the subject is a completely blank image.

Such suppression of the optotypes, in the perceived image, makes of course the determination of the refraction error of the non-dominant eye difficult, or even impossible. Even if the ocular dominance of the subject is not strong enough to cause such suppression, it often causes blinking or flickering of the image perceived by the subject. Besides, during such a binocular refraction protocol, a flickering of the image perceived by the subject may also be caused by vision problems of the subject related to ocular vergence. These adverse effects make the binocular refraction protocol less accurate, or less comfortable for the subject, and longer to be carried on.

SUMMARY OF THE INVENTION

One object of the disclosure is to provide a binocular refraction instrument, for determining at least one refraction feature of one or both eyes of a subject, in which the above mentioned detrimental effects, caused by ocular dominance and rivalry and/or by ocular vergence issues, are avoided or at least reduced.

The above object is achieved according to the invention by providing a binocular refraction instrument as defined by claim 1.

The inventors have observed that providing the two eyes of the subject with two different test images that comprise identical or similar peripheral images, induces a well balanced fusion of the left and right visual pathways. It results, for the subject, in a perceived image that is stable and that takes into account both the first and the second test images displayed to the subject, even in the central area of these test images, and even if the corresponding central images are markedly different.

Regarding ocular dominance/rivalry, one explanation for this improvement is that, as the visual system of the subject sees a left image and a right image that are mostly similar (thanks to said peripheral images), it perceives no contradiction between the left and right images and, thus, does not perform any selection between one or the other of the left and right visual pathways of the subject.

Regarding ocular vergence issues, one explanation for the stability/comfort improvement observed by the inventors is that it is easier for the visual system of the subject to stabilize gazing directions, or to have appropriate gazing directions, with the presence of the (substantially identical) peripheral images as a support than when a blank area surrounds the optotypes area.

Anyhow, providing the eyes of the subject with two test images as defined in claim 1 improves the stability of the binocular vision of the subject and makes the observation of these images more comfortable. So, when it is made use of such test images during a binocular refraction protocol, the subject assesses the refraction corrections to be tested/compared quicker and in more reliable manner than with conventional test images (without peripheral test images). The refraction corrections, appropriate to correct the subject's vision, are thus determined quicker, and more accurately.

Besides, for subjects whose ocular dominance is strong, thanks to the specific test images employed, the "suppression" phenomenon described above is avoided, and a binocular refraction protocol can thus be used to determine the refraction corrections appropriate to correct the subject's vision (which wouldn't have been possible with conventional test images).

According to an advantageous, optional feature, the control unit of the binocular refraction instrument is programmed so that the first test image, provided to the first eye of the subject, comprises a transition element which, for at least one image characteristic, provides a continuous transition from the first central image to the first peripheral image of the first test image.

And the control unit may be programmed so that the second test image, provided to the second eye of the subject, comprises also such a transition element which, for at least one image characteristic, provides a continuous transition from the second central image to the second peripheral image of the second test image.

The inventors have observed that such a transition element contributes to a well stabilized and balanced binocular vision, even if the first and second central images are markedly different.

One explanation for this effect is that, for the test image considered, the transition element enables to integrate gradually the central image within the peripheral image of the test image and links visually the central image to the peripheral image, from a visual point of view (the transition element enables the central image to blend in well the corresponding peripheral image). From a visual point of view, the test image then appears as a whole, constituted predominantly by the peripheral image (the central image appearing as a part of the peripheral image). So, with such transition elements, the visual perception of the subject mainly depends on the first and second peripheral images he sees, which, as already mentioned, have a stabilizing and balancing effect on the binocular vision of the subject (as they are mainly identical to each other). Fusion is thus more flexible, and double vision phenomenon, if existing, is less perceived and less inconvenient to the user.

The transition element of the first test image can be such that a quantity, representative of said at least one image characteristic, has the same value in the first central image and in the first peripheral image, or varies gradually from the first central image to the first peripheral image. And the same may apply to the transition element of the second test image. The at least one image characteristic mentioned above may comprise:
- an image luminosity;
- a color feature (a color value);
- an image element outer shape;
- a texture characteristic, such as a shape, orientation, size or density of the texture elements.

In a particular embodiment, the control unit of the binocular refraction instrument can be programmed so that the transition element comprises texture elements, said at least one image characteristic comprising a texture characteristic associated to said texture elements.

Besides, the control unit of the binocular refraction instrument can be programmed so that the first peripheral image, displayed to the first eye of the subject, represents an actual scene, object, or abstract figure as it would be seen from the position of the first eye of the subject, while the second peripheral image represents the same scene, object or abstract figure, as it would be seen from the position of the second eye of the subject. In other words, the first and second peripheral images could be stereoscopic images. In stereoscopic images, the different objects of the scene may be arranged to be located in different planes.

Optional, non-limiting features of the binocular refraction instrument are defined also, according to the invention, by claims 2 to 11. The above-mentioned objective is also achieved by providing a binocular refraction method as defined by claim 12, by providing a computer program as defined by claim 13, or by providing a set of test images as defined by claim 14.

The optional features of the binocular refraction instrument presented above can also be applied to the binocular refraction method, to the computer program, or to the set of test images defined respectively by claims 12, 13 and 14.

DETAILED DESCRIPTION OF EXAMPLE(S)

The following description with reference to the accompanying drawings will make it clear what the invention consists of and how it can be achieved. The invention is not limited to the embodiment/s illustrated in the drawings. Accordingly, it should be understood that where features mentioned in the claims are followed by reference signs, such signs are included solely for the purpose of enhancing the intelligibility of the claims and are in no way limiting on the scope of the claims.

BINOCULAR REFRACTION INSTRUMENT

Figure 1:
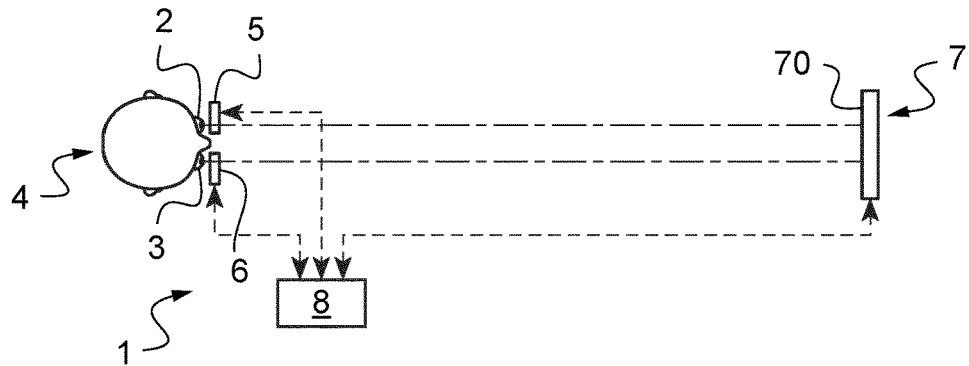
FIG. 1 represents schematically an embodiment of a binocular refraction instrument according to the invention.

FIG. 1 represents schematically, from above, the main elements of a binocular refraction instrument 1 for determining at least one refraction feature of a first eye 2 and/or of a second eye 3 of a subject 4, in a binocular manner, that is while the subject 4 has both eyes opened and un-obstructed.

The instrument 1 comprises a first optical unit 5, for providing the first eye 2 of the subject 4 with a first refraction correction, and a second optical unit 6 for providing the second eye 3 of the subject 4 with a second refraction correction.

The instrument comprises also an image display system 7 for providing a first test image 21, 51, 61, 71, 81 to the first eye 2 of a subject 4 and, at the same time, for providing a second test image 22, 52, 62, 72, 82 to the second eye 3 of the subject 4, the second test image being different from the first test image 21, 51, 61, 71, 81.

The first test image 21, 51, 61, 71, 81 is seen by the first eye 2 of the subject through the first optical unit 5, while the second test image 22, 52, 62, 72, 82 is seen by the second eye 3 of the subject 4 through the second optical unit 6.

In the embodiment of FIG. 1, each of the first and second optical units 5, 6 comprises a lens, a mirror, or a set of such optical components, that has adjustable refractive power features. For instance, the lens may comprise a deformable liquid lens having an adjustable shape. Alternatively, the optical unit may comprise an ensemble of non-deformable lenses having different optical powers, and a mechanical system that enables to select some of these lenses to group them to form the set of lenses through which the subject 4 can look. In this last case, to adjust the refractive power of the set of lenses, one or several lenses of the set of lenses are replaced by other lenses stored in the optical unit.

Each of these optical units 5, 6 is intended to be placed in front of one of the eyes 2, 3 of the subject, close to this eye (not further than a five centimeters, in practice), so that this eye 2, 3 can see a screen 70 of the image display system 7 through the lens, through the set of lenses, or by reflection onto a mirror of the optical unit 5, 6. The instrument is configured to enable refraction measurements at various distances (near vision, far vision and/or intermediate vision) and/or for various eye gaze directions (for example natural eye gaze direction lowered for reading, horizontal eye gaze direction for far vision). This screen 70 is located at a distance from the first and second optical units 5, 6 comprised between 25 cm (for near vision) and infinity when using a specific imaging system (not represented), such as a Badal system, or, if no imaging system is used (or using a plane mirror), up to about 8 meters in practice, or such as a system similar to the one disclosed in EP 3 298 952 allowing the combination of a first image provided by a screen (that could be constituted of one or more of peripheral image(s)), and a second image provided by an imaging module (that could be constituted of one or more of central images), both first and second images being possibly imaged at variable distances for the individual's eye.

The lens, the set of lenses, or the set of lenses and mirrors of the each of the first and second optical units 5, 6 has an overall spherical power S (spherical optical power, expressed for instance in diopters). And the cylindrical components of its refractive power are those of an equivalent cylindrical lens that has a cylindrical power C (expressed for instance in diopters), and whose cylinder has an orientation represented by an angle α. Each of the first and second refraction correction, provided by the corresponding optical unit 5, 6, may be characterized by the values of these three refractive power parameters S, C and α. This refractive correction could be equally characterized by the values of any other set of parameters representing the above mentioned refractive power features of the optical unit 5,6, such as the triplet {M, J0, J45}, where the equivalent sphere M is equal to the sphere S plus half of the cylinder C (M=S+C/2), and where J0 and J45 are the refractive powers of two Jackson crossed cylinders lenses representative of the cylindrical refractive power features of the lens or of the set of lenses of the optical unit 5, 6.

Regarding now the image display system 7, in the embodiment of FIG. 1, it is realized by means of a liquid-crystal display screen 70 that is able to display the first test image 21, 51, 61, 71, 81 with a first polarization, and, at the same time, to display the second image 22, 52, 62, 72, 82 with a second polarization. The first and second polarizations are orthogonal to each other. For instance, the first and second polarizations are both rectilinear and perpendicular to each other. Or, similarly, the first polarization is a left-hand circular polarization while the second polarization is a right-hand circular polarization.

The whole extent of the screen 70 can be seen through each of the first and second optical units 5, 6.

But the first optical unit 5 comprises a first polarizing filter that filters the light coming from the image display system 7. The first polarizing filter filters out the second polarization, and lets the first polarization passes through so that it can reach the first eye 2 of the subject. So, through the first optical unit 5, the first eye 2 of the subject can see the first image 21, 51, 61, 71, 81, but not the second image 22, 52, 62, 72, 82.

Similarly, the second optical unit comprises a second polarizing filter that filters the light coming from the image display system 7. The second polarizing filter filters out the first polarization, and lets the second polarization passes through so that it can reach the second eye 3 of the subject.

The image display system may use any other separation technic, such as «active»separation for which each image test is displayed alternatively at a high frequency while an electronic shutter synchronized is blocking the eye for which the image should not be addressed. Separation system could also use chromatic separation with chromatic filters both on the display and the eye in which each side/eye has different chromatic filters that block each other (for example red and green filters).

The first and second images (as represented on FIG. 2, for instance), coincide with each other (their respective frames coincide with each other), on the screen 70. They both fill the same zone, on this screen. Here, the screen 70 fills a part of the subject's field of view that is at least 5 degrees wide, or even at least 10 degrees wide.

As presented in detail below, each of the first and second test images to be displayed comprises:

a central image 21c, 51c, 61c, 71c, 81c, 22c, 52c, 62c, 72c, 82c for displaying optotypes (and that may, possibly, remain void in some cases), and a peripheral image 21p, 51p, 61p, 71p, 81p, 22p, 52p, 62p, 72p, 82p that surrounds the central image and contributes usefully to a well balanced fusion process between the left and right visual pathway, for the subject.

So, these test images 21, 51, 61, 71, 81, 22, 52, 62, 72, 82 are somehow composite images, and, besides, they comprise a peripheral image that is all the more stabilizing as the part of the field of view they occupy is wide. It is thus very useful to use a wide screen, as the one described above, to provide enough room to accommodate such composite images.

In alternative embodiments, the image display system may be implemented by means of a reflective, passive screen (such as an aluminum-foil screen) and one or several projectors for projecting onto this screen the first test image, with the first polarization, and the second test image, with the second polarization, the first and second test images being superimposed to each other, on the screen.

Still, in other embodiments, the image display system may comprise a first display screen to provide one of the test images to the first eye of the subject, and a second display screen, distinct from the first one, to provide another of the test images to the second eye of the subject (instead of employing a single screen but two different polarizations). In this case, the first and second optical units may be achieved, for instance, by means of a first and a second Badal-like systems, placed respectively in front of the first eye, and in front of the second eye of the subject. Each of these Badal-like systems would comprise at least one lens, and a displacement system to modify a length of an optical path that joins this lens to the display screen considered, in order to form an image of this display screen at a distance from the eye of the subject that is adjustable. In such a case the first (respectively second) refraction corrections provided by the first (respectively second) optical unit is directly related to the distance at which it forms the image of the first (respectively second) display screen. The spherical refractive correction provided by this optical unit, for instance, is equal or approximately equal to the inverse of the algebraic distance between the eye 4 of the subject and the image of the display screen formed by the optical unit.

Anyhow, the first and second refraction corrections provided by the first and second optical units 5, 6 are adjustable. These refraction corrections are controlled by a control unit 8 of the instrument 1.

The control unit 8, that comprises at least one processor and at least one non-volatile memory, is programmed to pilot the binocular refraction instrument 1 in order to implement one or several of the binocular refraction methods described below (in the section entitled "binocular refraction methods"). These binocular refraction methods have in common that the subject 4 has both eyes opened, and that the specifically designed first 21, 51, 61, 71, 81 and second test images 22, 52, 62, 72, 82 mentioned above are provided, respectively to the first eye 2 and to the second eye 3 of the subject, during at least a part of the refraction method.

More precisely, during each of these methods, the first and second test images provided to the subject are as follow:

the first test image 21, 51, 61, 71, 81 comprises the first central image 21c, 51c, 61c, 71c, 81c surrounded by the first peripheral image 21p, 51p, 61p, 71p, 81p, and the second test image 22, 52, 62, 72, 82 comprises the second central image 22c, 52c, 62c, 72c, 82c surrounded by the second peripheral image 22p, 52p, 62p, 72p, 82p, as mentioned above;

each of the first and second peripheral images is non-uniform, and a level of similarity between the first and second peripheral images is higher than a given threshold;

the first central image 21c, 51c, 61c, 71c, 81c comprises at least one first optotype 21o, 51o, 61o, 71o, 81o; and the second central image 22c, 52c, 62c, 72c, 82c is different from the first central image 21c, 51c, 61c, 71c, 81c, the second central image 22c, 52c, 62c, 72c, 82c being deprived of optotype or comprising only one or several second optotypes 22o, 82o that have a contrast or sharpness level smaller than a contrast or sharpness level of said at least one first optotype 21o, 51o, 61o, 71o, 81o.

As explained above in the section presenting a "summary of the invention", making use of such first and second test images improves the stability of the binocular vision of the subject 4 and makes the observation of these images more comfortable, avoiding blinking or flickering of the global image perceived by the subject (after fusion), and limiting ocular vergence issues. A binocular refraction method in which such images are provided to the subject, can thus be carried on faster than when conventional binocular test images are used, and leads to more accurate results.

Besides, when these test images are employed, no "suppression" phenomenon is observed, even for subjects whose ocular dominance is strong. In other words, the at least one first optotype of the first test image remains perceptible in the global, binocular image perceived by the subject (after neural fusion between the left and right visual pathways). So, thanks to the test images employed, a binocular refraction method can be used to determine the refraction corrections appropriate to correct the subject's vision, even if the ocular dominance of the subject is strong (which wouldn't have been possible with conventional test images, with no peripheral images).

A first, second, third, fourth and fifth couples of test images, each comprising a first test image 21, 51, 61, 71, 81 and a second test image 22, 52, 62, 72, 82 having the characteristics mentioned above, are described below (in reference to FIGS. 2 to 8), in the section entitled "binocular test images".

In the embodiment of the binocular refraction instrument 1 described here, one or several of these couples of test images are stored in the memory of the control unit 8, so that they can be displayed by the image display system 7 when a binocular refraction method is carried on by means of the binocular refraction instrument 1 described above. More generally, at least one computer program is stored in this memory, this computer program comprising instructions which, when the program is executed by the control unit 8, cause the binocular refraction instrument 1 to carry out a binocular refraction method having the features presented above (like the methods described in detail below). This computer program comprises data representative of at least one of these couples of test images.

Binocular Test Images

Two main types of binocular refraction methods, and associated sets of test images, are described below.

Figure 2:
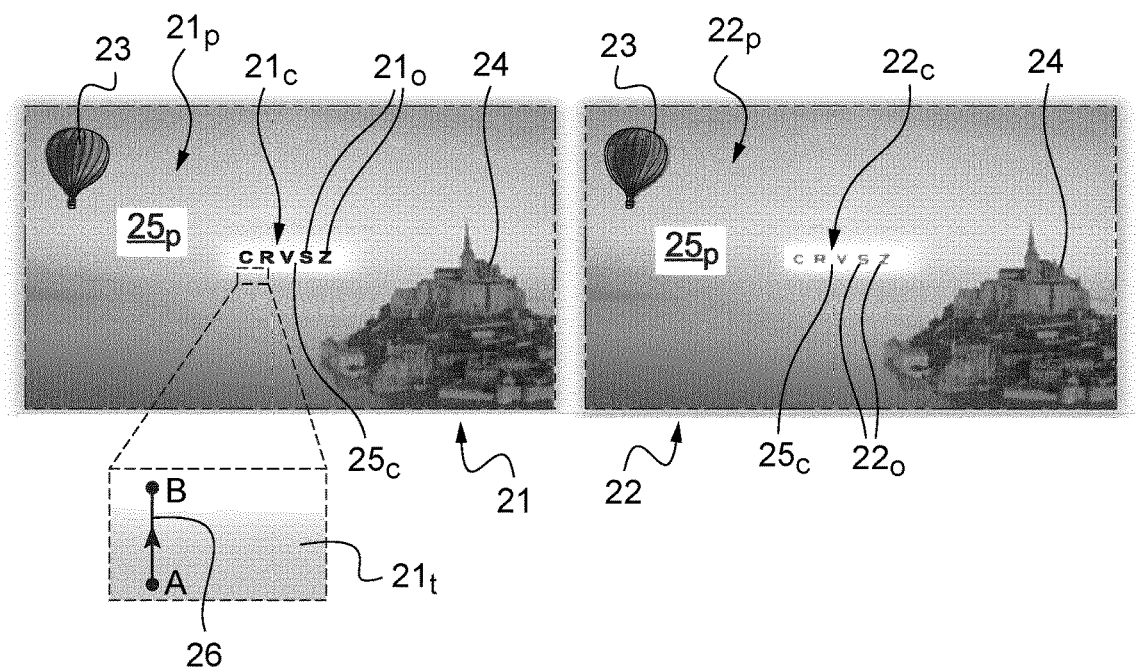
FIG. 2 represents schematically a first couple of test images, comprising a first test image and a second test image, to be provided respectively to a first eye and to a second eye of the subject by the binocular refraction instrument of FIG. 1.

In the binocular refraction methods of the first type, the eyes 2, 3 of the subject 4 are provided only one at a time with a test image in which one or more sharp and well contrasted optotype can be perceived (like in the first test image 21 of FIG. 2, for example), while the other eye is provided with a test image deprived of optotypes or comprising only one or more optotypes that have a reduced contrast or sharpness level (like the second test image 22 of FIG. 2).

The first, second, third and fourth couples of test images, represented in FIGS. 2, 5, 6 and 7 respectively, are examples of couples of test images suitable for a binocular refraction method of this first type.

In such a binocular refraction method, the first refraction correction and the second refraction correction, provided to the first eye 2 and to the second eye 3 of the subject respectively, are assessed by the subject alternatively, one at a time, as his/her eyes are provided only one at a time with optotypes that can be sharply perceived. The first and second refraction methods described below, in reference to FIGS. 9 to 12, belong to this first type of refraction methods.

Figure 8:
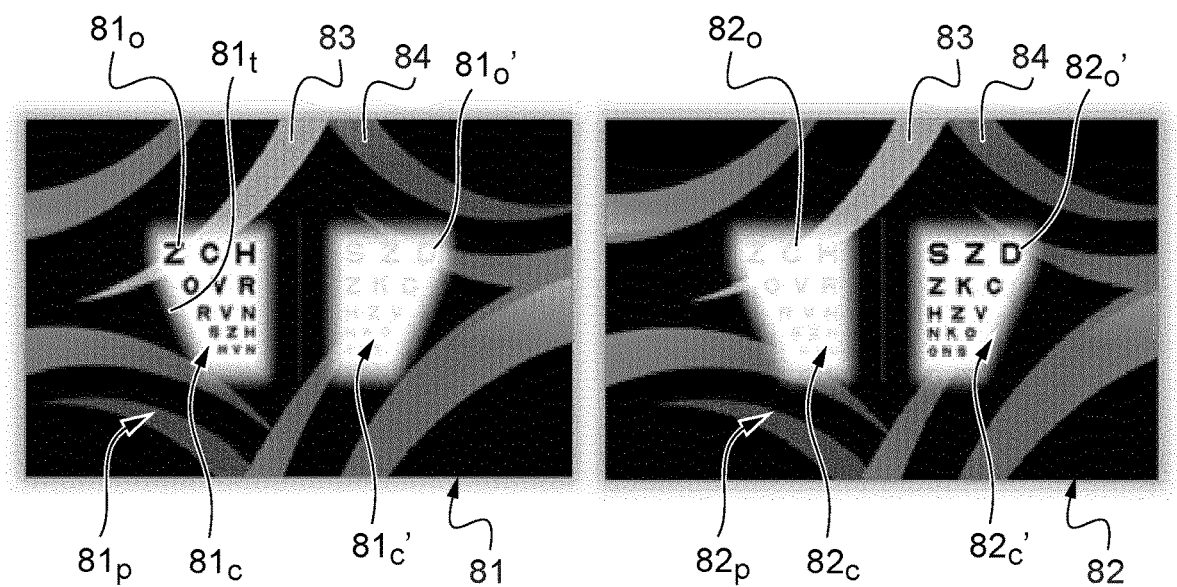

In the binocular refraction methods of the second type, a first test image 81 and a second test image 82 that both comprise at least one sharp and well contrasted optotype, are provided to the first eye 2 and to the second eye 3 of the subject 4 respectively (FIG. 8). But the sharp and well contrasted optotype or optotypes 81o present in the first test image 81, and the ones 82o' present in the second test image 82 are displayed in different parts (81c, 82c') of the subject's field of view. So, in a binocular refraction method of the second type, the first and second refraction corrections can be assessed simultaneously by the subject.

A set of test images to be used in a refraction method of the second type may comprise, for instance, a first and a second test images each of which comprising two distinct, disconnected central images 81c, 81c'; 82c, 82c', surrounded by a peripheral image 81p, 82p, like in the first and second test images 81, 82 of FIG. 8.

Figure 13:
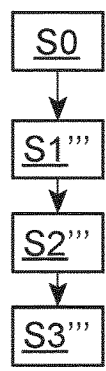
FIGS. 13 and 14 represent schematically some steps of a third binocular refraction method carried on by means of the binocular refraction instrument of FIG. 1.

The third binocular refraction method described below in reference to FIGS. 13 and 14 belongs to this second type of binocular refraction methods. But, whatever the type of binocular refraction method considered, in each the exemplary couples of test images described below, the first test image 21, 51, 61, 71, 81 comprises a first transition element 21t, 51t, 71t, 81t, which, for at least one image characteristic, provides a continuous transition from the first central image 21c, 51c, 61c, 71c, 81c to the first peripheral image 21p, 51p, 61p, 71p, 81p of the first test image.

As explained above in the section presenting the "summary of the invention", such transition elements, which enable a visual integration of the first central image into the corresponding peripheral image and avoids an abrupt discontinuity between them, contributes efficiently to the stabilization of the binocular vision of the subject 4.

Similarly, in each of these couples of test images, the second test image 22, 52, 62, 72, 82 comprises a second transition element 22t, 52t, 72t, 82t, which, for at least one image characteristic, provides a continuous transition from the second central image 22c, 52c, 62c, 72c, 82c to the second peripheral image 22p, 52p, 62p, 72p, 82p of the second test image.

More specifically, for the couples of test images described here, the first transition element 21t, 51t, 71t, 81t is such that a quantity, representative of said image characteristic, has the same value in the first central image and in the first peripheral image, or varies gradually from the first central image to the first peripheral image. And the same may apply to the second transition element 22t, 52t, 72t, 82t of the second test image.

In the case of the first, second, third and fifth couples of test images, the image characteristic for which the transition from the central image to the peripheral image is continuous is an image luminosity L. In these cases, the image luminosity L varies gradually from the central image considered, to the peripheral image that surrounds it (FIGS. 2, 5, 6 and 8).

In the case of the fourth couple of test images (FIG. 7), the image characteristic, for which the transition from the central image to the peripheral image is continuous, is the outer shape of an element represented in the test image. More precisely, in this case, the outer shape of the central image 71c, 72c is the same as the outer shape of an element 77 (here a paraglider wing) represented in the first peripheral image 71p, 72p.

The first, second, third, fourth, and fifth couples of test images, whose general characteristics have been presented above, can now be described in more detail, one after each other.

Figure 3:
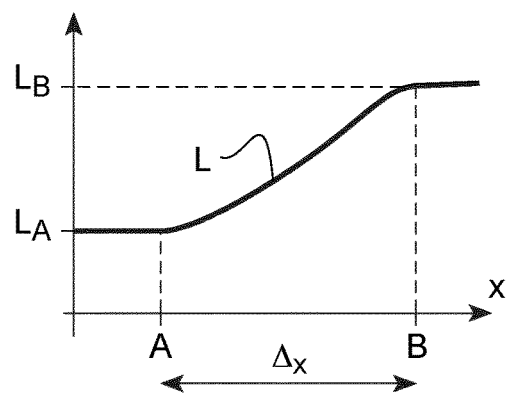
FIG. 3 represents schematically the variation of the image luminosity in a part of the first test image of FIG. 2.
Figure 4:
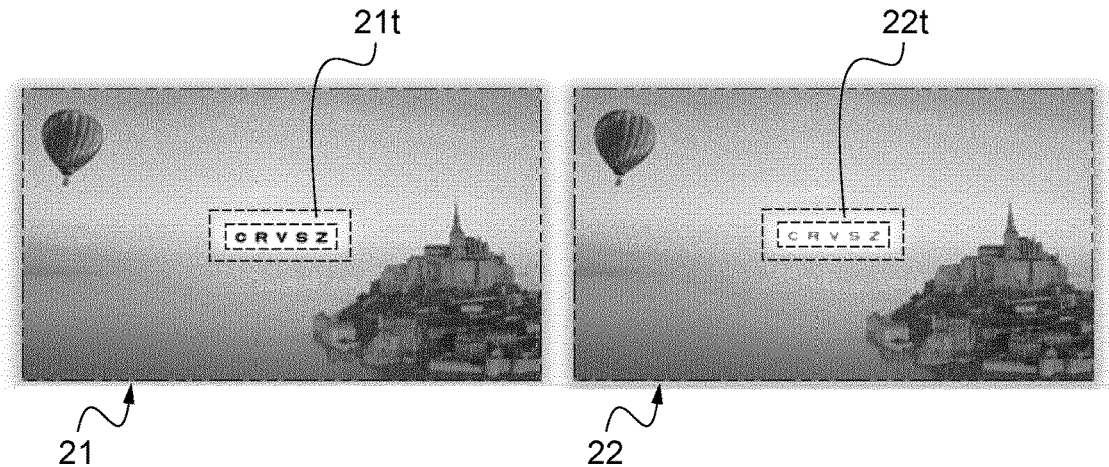
FIG. 4 represents again the first and second test images of FIG. 2, to identify more distinctly a first transition element and a second transition element present in the test images represented.

First Couple of Test Images (FIGS. 2 to 4)

First Test Image 21

The first central image 21c of this first test image 21 has a rectangular shape. It has a background 25c that is homogeneous, white and luminous. The image luminosity in any point of the central background 25c may for instance equal the highest luminosity in the first test image 21, or may be higher than three fourth of the highest luminosity in the first test image.

First optotypes 21o are superimposed over the central background 25c, which, as represented, are Snellen-letters, namely a "C", an "R", a "V", an "S" and a "Z".

In a variant, other kinds of optotypes could be employed, instead of such letters. Here, the term "optotype" designate a symbol (that is to say a figure) or a set of symbols appropriate to test the clarity/sharpness of the vision of the subject 4. It may be a symbol, like a Snellen letter, appropriate to determine whether the tested eye is well-corrected regarding spherical refraction. It can also be a symbol appropriate to characterize astigmatism, like a "clock astigmatism chart" comprising a triplet of parallel lines for each hour of clock dial. Generally, an optotype is a symbol or a set of symbols, each of which delineated by a closed outline and homogeneously filled, for instance black-filled or grey-filled. The symbol is superimposed onto a background, generally white or grey (in the case of "vanishing" optotypes), distinct from the filling of the symbol itself. Each symbol is rather small, or thin, from an angular point of view. Its angular width is generally smaller than one degree, typically of tenth of a degree.

The optotypes employed could be Snellen or any other letters, Arabic or Chinese characters, Landholt Cs, figures of the Lea pediatric test, figures of the GolovinpSivtsev table, or sets of lines or points for testing astigmatism (like in FIG. 5), instead of the Snellen letters represented in FIG. 2.

The first optotypes 21o are well contrasted. Their contrast is higher that 50%, and even higher than 80%. The contrast of optotypes is defined as the ratio (Lmax−Lmin)/(Lmax+Lmin), where Lmax is the maximal luminosity in the surrounding of the optotype, here the luminosity of the central background 25c, whereas Lmin is the minimal luminosity within the optotype, here the luminosity of the black filling of the optotype. Alternatively, the image and optotypes could be of inverse contrast (white symbols on dark background) with peripheral image representing a scene at night.

The first optotypes 21o are sharp. Their outline is well defined. In practice, the thickness of the outline of such perfectly sharp optotypes, that is to say the width of the transition zone between the homogeneous filling of the optotype and the surrounding of the optotype, is smaller than 0.2 or even 0.1 of the optotype width.

The area of the first central image 21c is smaller than the area of the first peripheral image 21p. More precisely, a ratio of the area of the first central image 21c, by the area of the first peripheral image 21p is smaller than one third, and even smaller than 5%, here. The predominance of the peripheral image 21p over the central image 21c, in terms of area, is beneficial, as the peripheral image is responsible for the stabilizing effect mentioned above, and compensates for the differences between the first and second central images 21c, 22c, from a visual point of view.

The first central image 21c occupies a central part of the first test image 21. The first central image 21c does not extend till the edge of the first test image, and is surrounded all around by the first peripheral image 21p.

The first peripheral image 21p fills the part of the first test image 21 that is not occupied by the first central image 21c. The first peripheral image 21p is an image of a landscape, comprising an image of a hot-air balloon 23 and an image of a hill 24 with constructions on it. In the first test image 21, this hill 24 appears further than the balloon 23, for an observer of the first test image 21 (the hill is represented at a smaller scale than the balloon). The background 25p of the first peripheral image 21p, designated as the peripheral background 25p, is constituted of some blue sky, of moderate luminosity, rather homogeneous.

More generally, the first peripheral image 21p is non-uniform. It comprises several distinct elements representing objects (like the balloon 23), abstract graphical structures (like the crescents 83 and 84 represented in FIG. 8), or landscape elements (like the hill 24). The spatial frequency content of the first peripheral image 21p extends at least till a given spatial frequency threshold. This spatial frequency threshold is equal to 2 line pairs per degree, for instance, or is even equal to 4 or to 10 line pairs per degree when the image is seen from the subject's position (the rib of the balloon 23, for instance, or small constructions details on the hill 24, are zones with a high spatial frequency content, in FIG. 2). The spatial frequency threshold mentioned above may be equal or higher than 1 line pair per optotype, for instance.

The rich and diversified visual content of the first peripheral image 21p contributes to the stabilizing effect of this image. Indeed, it provides an abundant visual support, identical or similar to the one present in the second peripheral image 22p, which enables a very stable and well-balanced fusion between the left and right visual pathways of the subject. It helps focusing and fusion because the stereoscopic scene may bring elements of perception for monocular and binocular distances which enable the visual system to stabilize. Besides, it captures the attention of the subject, from a visual point of view and helps maintaining the subject focused on the test images provided to him/her.

The first central image 21c extends in a part of the first test image 21 where one would expect to see the peripheral background 25p to extend (so, here, some blue sky), in the absence of the first central image 21c.

For the first test image 21 represented in FIG. 2, the first transition element 21t, which provides a continuous transition from the first central image 21c to the first peripheral image 21p, is the border of the first central image 21c.

This border 21t is thick, and, across it, the image luminosity L varies gradually. This thick border 21t is identified in FIG. 4: in this figure, the border 21t extends between the two dashed rectangular frames.

The insert of FIG. 2 shows a part of this shaded, thick border 21t in an enlarged manner. In this insert, a point A, located in the peripheral background 25p, and a point B, located in the central background 25c, are represented.

In point A, the image luminosity L has a peripheral luminosity value $L_A$. This value is representative of (for instance equal to) an average image luminosity of the peripheral background 25p, in the surrounding of the first central image. In point B, the image luminosity L has a central luminosity value $L_B$. This central luminosity value $L_B$ is the value of the image luminosity in the central background 25c, which, here, is homogeneous. The peripheral and central luminosity values $L_A$ and $L_B$ are different from each other. In this example, the luminosity difference $\Delta L$ between the peripheral luminosity value $L_A$ and the central luminosity value $L_B$ is approximately equal to 10% of the central luminosity value.

FIG. 3 represents the variations of the image luminosity L along a line 26 traversing the border 21t perpendicularly to the border. This line 26 links point A to point B. As it can be seen in this figure, along this line, the image luminosity L varies gradually and monotonically (here, it increases) from the peripheral luminosity value $L_A$ to the central luminosity value $L_B$.

The thickness $\Delta x$ of the border 21t is the distance over which the image luminosity L varies from the peripheral luminosity value $L_A$ to the central luminosity value $L_B$, along a line traversing the border 21t perpendicularly to the border, like the line 26 represented in FIG. 2. This thickness $\Delta x$ may be equal or higher than the width of one of the first optotypes 21o of the first central image. Alternatively, this thickness $\Delta x$ may be adjusted as a function of the visual task difficulty (if a task is complicated, a thicker border is advantageous to enable the subject to maintain his/her attention on the test).

Within this thick border 21t, the absolute value of the gradient of the image luminosity, $\delta L/\delta x$, is larger than the luminosity difference $\Delta L$ divided by the total thickness of the border. In the image luminosity gradient $\delta L/\delta x$, x is the angular position of the point of the image considered, as seen from the subject's position.

In the case of FIG. 2, the image characteristic, for which the transition from the first peripheral image 21p to the first central image 21c is made continuous by the first transition element 21t, is the image luminosity L.

Still, in a variant, the image characteristic, for which the transition from the first peripheral image to the first central image would be continuous, could be a color feature, for instance, instead of the image luminosity L. So, for example, the image saturation, that is to say the ratio of the image chroma to its luminosity, may be different in the peripheral background than in the central background, and may vary gradually and monotonically from a peripheral saturation value to a central saturation value. In this case, the color of the peripheral background could be a very pure, colorful bleu, for instance, while the central background is grey. In such a case, the image luminosity could be the same in the peripheral background as in the central background.

Second Test Image

The second test image 22 is very similar to the first test image 21, except concerning the second central image 22c, which is different from the first central image 21c. Indeed, the second central image 22c comprises only second optotypes 22o that have a contrast and/or sharpness level smaller than the first optotypes 21o of the first central image 21c.

The second optotypes 22o have a reduced contrast/sharpness because this couple of test images 21, 22 is intended for testing the acuity and/or refraction defects of the subject one eye after the other. For instance, when the first test image 21 is provided to the first eye 2 of the subject while the second test image 22 is provided to the second eye 3 of the subject, it is solely the acuity and/or refraction defects of the first eye of the subject that is tested, yet in a binocular way.

Figure 5:
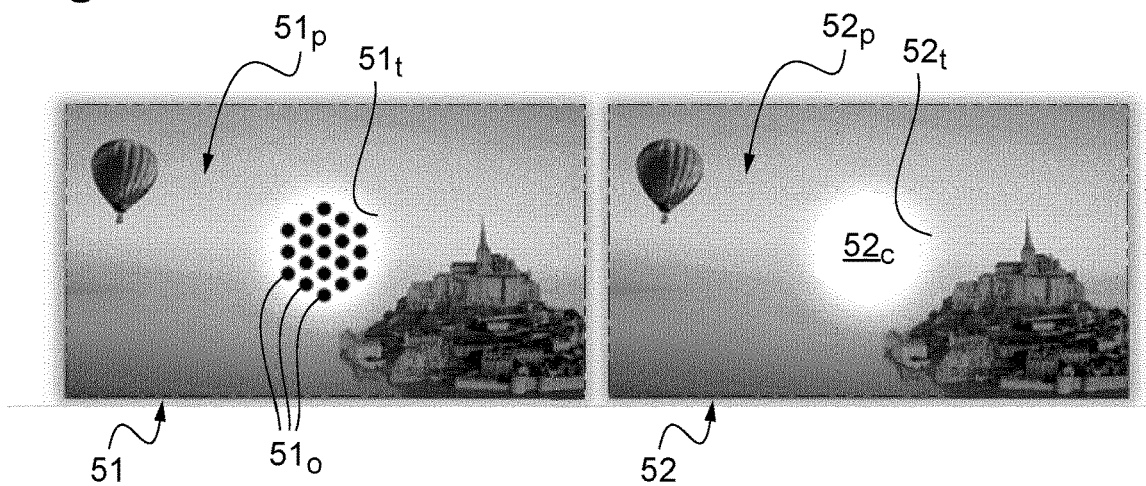
FIGS. 5, 6, 7 and 8 represent schematically a second, a third, a fourth and a fifth couples of test images, each comprising a first test image and a second test image to be provided to the first eye and to the second eye of the subject respectively.
Figure 6:
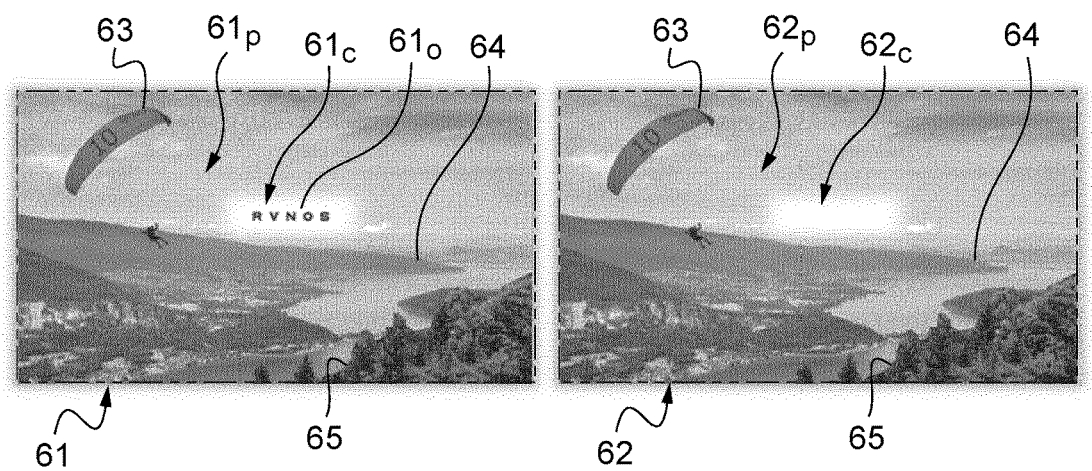

So, it is clear that the second optotypes 22o could be omitted, in a more basic variant (like it is the case for the second and third couples of test images of FIGS. 5 and 6, for instance).

Yet, for the subject, the presence of these low contrast and/or low sharpness second optotypes 22o in the second central image 22c leads to an even better balanced and stable binocular vision, with no "suppression" of the first optotypes in the global image perceived by the subject after fusion between the left and right visual pathways.

Indeed, apart from their contrast or sharpness, the second optotypes 22o are identical to the first optotypes 21o: their shapes, sizes, positions and orientations within the second test image 22 are the same as the shapes, sizes, positions and orientations of the first optotypes within the first test image 21. In the case of FIG. 2, the second optotypes 22o are Snellen letters, identical to the ones present in the first central image 21c (except from their sharpness/contrast), namely a "C", an "R", a "V", an "S" and a "Z".

Compared to a second central image deprived of optotype, the presence of these second optotypes 22o, reduces the difference between the first test image 21 and the second test image 22, while still allowing to test the subject's vision in a binocular manner, and one eye at a time (as the second optotypes cannot be sharply perceived by the subject).

And as already discussed, reducing the differences between the first test image 21 and the second test image 22 contributes to a well balanced binocular vision.

In other words, the first and second optotypes 21o, 22o are some kinds of first and second balancing elements, present in the first central image and in the second central image respectively, which, due to their similarity, create a visual link between these two central images 21c, 22c. And this visual link contributes to a well-balanced visual fusion process.

Regarding the contrast and sharpness level of the second optotypes, one of them at least is small enough to cause an acuity decrease by a factor of 2 at least for the eye provided with the second test image 22, compared to optotypes perfectly sharp and having a contrast of 100 percent.

Let suppose for instance that the eye provided with the second test image 22 is properly corrected by its optical unit 5, 6, thus having a visual acuity of 10/10 or higher (once corrected). Then, the contrast or sharpness level of the second optotypes 22o is small enough to reduce the effective acuity of the subject to 5/10. That is to say that the contrast or sharpness level of the second optotypes 22o is so small that these optotypes can be identified by the subject only if they are large enough (from an angular point of view), namely larger or as large as optotypes of a standard visual test chart corresponding to a 5/10 acuity.

During the binocular refraction methods described below, in reference to FIGS. 9 to 12, one of the eyes of the subject is the "working" eye. This eye is provided with well-contrasted and sharp optotypes, like the first ones 21o, in order to determine a refraction correction appropriate to correct optimally the refraction defects of this eye. Meanwhile, the other eye of the subject, designated as "the fellow eye", looks at a test image with no sharp or well-contrasted optotype, like the second test image 22. During such a refraction method, the working eye is usually blurred, that is to say fogged, by adding additional positive diopters to a starting correction. Then, this eye is defogged step by step until the subject is able to identify small optotypes, corresponding to a 10/10, or even higher acuity. During such a process, the acuity of the working eye, corrected by these different refraction corrections, varies approximately from 6/10 or 7/10 (when fogged) to 10/10 or higher (when defogged).

Regarding the second optotypes 22o, as explained above, their contrast/sharpness is small enough so that the effective acuity, with which the fellow eye can see them, is equal to or smaller than 5/10, whatever the refraction correction of the fellow eye.

So, the presence of these second optotypes 22o does not disturb the determination of the appropriate refraction correction of the working eye. Indeed, the subject can identify small, "10/10 visual acuity" optotypes, displayed to the working eye, only if this eye is properly corrected (as the second optotypes cannot be sharply perceived). And during the fogging/defogging process of the working eye, the optotypes sharpness perceived by the subject, in the global image he/she perceives, is the one of the first optotypes 21o, as the second optotypes can only be perceived with a sharpness smaller than the first ones.

In practice, to obtain the visual acuity decrease by a factor of 2 for the optotypes of the second test image, second optotypes 22o perfectly sharp but having a contrast of 10% only could be employed, for instance.

Alternatively, to obtain such an acuity decrease, the second optotypes could have a contrast of 100% while being blurred, as if they would have been seen through a blurring lens having a spherical refractive power +1 diopter higher than a spherical refractive power optimally correcting the eye considered. Such optotypes, blurred "as if they would have been seen through such a blurring lens", can be precalculated by means of an optical simulation. During such a numerical optical simulation, they can be obtained, for instance, as the image of perfectly sharp optotypes by a simulation lens located several meters away from these optotypes and having a spherical refractive power equal to Po+1 diopters (where Po may be equal to a few tens of diopters, for instance), this image being formed on a simulation screen located 1/Po meters behind the lens.

More details regarding how to adjust the contrast and/or sharpness level of the second optotypes (or equivalently, their contrast and/or blur level), as a function of the visual acuity reduction to be obtained, can be found in the following document: "Effects of Luminance, Contrast, and Blur on Visual Acuity", by C. A. Johnson and E. J. Casson, in Optometry and Vision Science, January 1996, pages 864 to 869, in particular in FIGS. 3 and 4 of this document.

Apart from this contrast/sharpness difference between the first and second optotypes, the first and second central images 21c, 22c are identical, here (same size, same central background 25c).

Regarding now the second peripheral image 22p, in the case of FIG. 2, it is completely identical to the first peripheral image 21p. The second transition element 22t is also identical to the first transition element 21t of the first test image 21. It is noted however that, alternatively, the first and second peripheral images could be very similar from each other, yet not completely identical for example to enable a stereoscopic 3-D rendering of the scene represented. Still, in such a case, the first and second peripheral images would be similar enough that a level of similarity between them is higher than a given threshold.

This level of similarity could for instance be equal to a normalized correlation product between the first peripheral image and the second peripheral image, that is to say equal to the correlation product between them, divided the square root of the product of the autocorrelation of the first peripheral image by the autocorrelation of the second peripheral image. In such a case, the level of similarity threshold mentioned above could be equal to 0.8, for instance.

The level of similarity could also be defined, between two images identical in size/shape/color, as an angular deviation of less than 6° when observed by a subject at far vision distance, or as a difference of less than +/− 1 diopter.

More generally, the level of similarity threshold could be equal to 0.8times a reference level of similarity, this reference level of similarity being a level of similarity between the first peripheral image and the first image itself, computed in the same manner as the level of similarity between the first and second peripheral images (except that it concerns the first peripheral image only).

Alternatively, the level of similarity threshold could be equal to 10 times a level of similarity computed between the first image and a random image.

The admissible range of level of similarity can be defined empirically by showing to a subject successive combinations of two images with the same first reference image and different second images differing each from the first reference image and from another, and defining each with the first reference image a particular level of similarity. The lower limit of the admissible range of level of similarity will correspond to the highest level of similarity at which a subject cannot perceive a stereoscopic 3D rendering of the scene represented. The upper limit of the admissible range of level of similarity will correspond to the lowest level of similarity at which a subject will complain of double vision.

Second Couple of Test Images (FIG. 5)

The second couple of test images is identical to the first couple of test images, except that:
  the second central image 52c is deprived of optotypes;
  the first and second central images 51c, 52c are circular, disc-shaped, instead of being rectangular;
  the first optotypes 51o are small black disks, instead of Snellen letters; these disks being displayed so as to form a triangular lattice, whose external shape is an hexagon.

This set of first optotypes 51o is well-suited to test astigmatism features of the eye provided with this first test image 51.

Third Couple of Test Images (FIG. 6)

The third couple of test images is identical to the first couple of test images, except that:
  the second central image 62c is deprived of optotypes;
  the first optotypes 61c are different Snellen letters than for the first couple of test images, namely an "R", a "V", an "N", an "O" and an "S";
  the landscape represented in the first and second peripheral images 61p, 62p is different from the one represented in the first and second peripheral images 21p, 22p of the first couple.

The landscape represented in the first and second peripheral images 61p, 62p comprises:
  some trees 65 in the foreground,
  on one side of the image 61p, a paraglider 63,
  a lake and hills; and in the horizon, on another side of the image 61p, opposite the paraglider 63, a cape 64.

The background is, again, mainly constituted by some blue sky. The paraglider is oriented as if moving towards the distant cape 64.

Such an arrangement maintains the subject focused on the image he perceived. Indeed, when looking at such a scene, the subjects tends to look at the paraglider, and then to look in the direction that the paraglider seems to follow, namely towards the cape 64. The subject thus tends to explore the whole landscape, from the paraglider 63 to the cape 64, and back, which maintains efficiently the subject's attention, from a visual point of view.

This first peripheral image 61p is an example of an image having a narrative content, that is to say an image representing a scene in which some elements (here the paraglider 63) are clearly elements that would move across the scene, in the actual scene, and/or that comprises different elements related one to the other, from a visual point of view (here, for example, the paraglider, the lake and the cape are related one to the other by the direction of movement of the paraglider).

For instance, an image comprising several hot-air balloons, arranged as if they were following each other, forming a line directed toward the summit of a mountain, is an image having a rich narrative content.

As explained above, images having a narrative content are useful in a refraction protocol, as they help to maintain the subject focused on the images provided to him/her.

Moreover, in this embodiment, the background chosen represents natural environments divided into different planes implying for the subject different depth of observation (on the FIG. 6, from the front to the back of the stereoscopic image: some trees 65 in the foreground, the paraglider 63, a lake and hills and in the horizon, a cape 64, some blue sky as the background).

Such background attempts to reduce the subjects' stress since looking at an environment that seems the most natural since constituted by different elements appearing as being placed on different planes. This background has been divided into different planes, with increasing disparities, so that the monocular depth indices and the stereoscopy give congruent information. The depth indices were considered and taken into account when designing the images.

Of course, other kinds of natural environment can be used such as sunflower field, or lavender field divided in different planes of observation such as from the front to the back of the stereoscopic image:
  specific sunflower or lavender twig perceived closer to the subject
  different portion of the sunflower/lavender field positioned at increasing depth of observation
  one or several tree(s) in an intermediate plane of the sunflower/lavender field
  one or several kite flying in the sky at different depth of observation mountains chain in the deeper background of the lavender/sunflower field the blue sky at the background.

Figure 7:
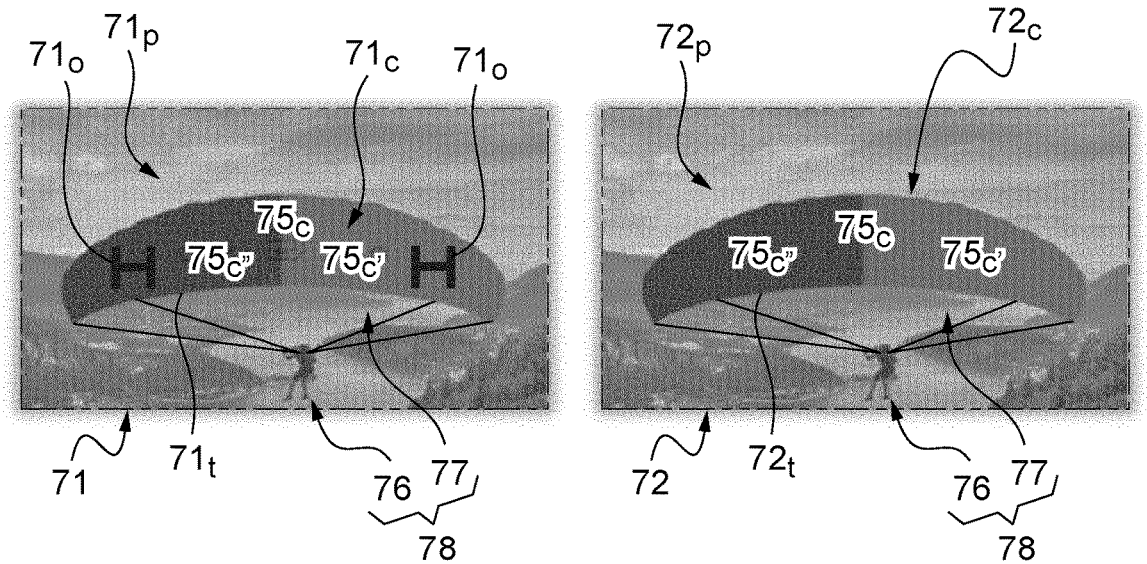

Fourth Couple of Test Images (FIG. 7)

The fourth couple of test images is quite different from the previous ones.

It enables to carry on a Green/Red duochrome test, for a fine adjustment of the spherical refraction correction provided to one of the eyes of the subject.

So, for this fourth couple of test images, each of the first and second central images 71c, 72c has a central background 75c that comprises two homogeneous parts. This central background 75c comprises:

a first background part 75c', homogeneously filled with green, and
  a second background part 75c', homogeneously filled with red.

The second central image 72c is deprived of optotypes.

The first central image 71c comprises first optotypes 71o that are Snellen letters, here an "H" and an "O". The same optotypes are superimposed on the first background part 75c', and on the second background part 75c'. So, here, an "H" is superimposed on the first background part 75c', and another "H", identical to the first one, is superimposed on the second background part 75c'.

Except concerning optotypes, the first and second central images 71c, 72c are identical to each other.

The first and second peripheral images 71p, 72p are identical to each other. They represent a landscape with a paraglider 78 in the foreground, a lake, hills, and some blue sky in the background. The paraglider 78 comprises a wing 77, hangers, and a seat 76 in which the paraglider's pilot is seating.

The ratio of the area of the first central image 71c, by the area of the first peripheral image 71p is smaller than one third (and the same applies to the second test image 72).

For this fourth couple of test images, the transition element between the first peripheral image 71p and the first central image 71c is, again, the border 71t of the central background 75c. But contrary to the previous couples of test images, this border 71t is sharp instead of being blurred and gradual.

However, the border 71t of the central background 75c matches the outline of the wing 77 of the paraglider 78. So, the first central image 71c is somehow inserted in the first peripheral image, precisely replacing the image of a part (here the paraglider wing 77) of an object (here the complete paraglider 78) that is represented in the first peripheral image 71. Indeed, the outline of the image of the part of this object 78 coincides with the border 71t of the central background 75c.

The first central image 71c thus appears as being part of the object 78 represented in the first peripheral image 71p. So, the subject perceives the first image 71 as a whole, occupied mainly by the first peripheral image 71p, which has a stabilizing and balancing effect, as explained above.

In this case, the continuity between the first central image 71c and the first peripheral image 71p, provided by the transition element 71t, is a continuity of shape, the central background 75c and the paraglider wing 77 having the same outer shape, and, even, the same outline. So, in this case, formally, the quantity for which the transition is continuous is a quantity representative of an image element outer shape, the image elements considered being, for the first central image, its background 75c, and, for the first peripheral image, the paraglider wing 77. The quantity representative of the outer shape of these image elements could be, for instance, a set of bidimensional coordinates of different points distributed along the outline of the image element considered.

In the second test image 72, the second transition element 72t is identical to the first transition element 71t: it is constituted by the mutual outline 72t of the central background 75c and of the paraglider wing 77.

Complementarily, it is possible to add texture elements not only on the outline but also inside the wing representing shadow due to the shape of the wing, thus increasing the link between the peripheral image and the central image.

Fifth Couple of Test Images (FIG. 8)

As already mentioned, for this couple of test images, both the first test image 81 and the second test image 82 comprise at least one sharp and well contrasted optotype 81o, 82o' ("Z C H" for the first test image 81, and "S Z D" for the second test image 82, see FIG. 8), displayed in different parts (81c, 82c') of the subject's field of view, to enable a simultaneous assessment of the first and second refraction corrections provided respectively to the first 2 and to the second eye 3 of the subject.

More specifically, the first test image 81 comprises two distinct, disconnected central images, namely the first central image 81c and an additional first central image 81c', both surrounded by the first peripheral image 81p. And the second test image 82 comprises also two distinct, disconnected central images, namely the second central image 82c and an additional second central image 82c', both surrounded by the second peripheral image 82p.

The first and second central images 81c, 82c coincide with each other, and the additional first and second central images 81c', 82c' coincide also with each other, when the first and second test images are superimposed to each other (with their respective frames coinciding).

The first central images 81c is located in a central part of the first test image 81, but on the left, while the additional first central image 81c' is located in a central part of the first test image 81, but on the right.

Like for the first couple of test images, the first central image 81c comprises sharp and well contrasted first optotypes 81o while the second central image 82c comprises optotypes 82o having a reduced contrast and/or sharpness level. The sharpness and contrast of these different optotypes are the same as for the corresponding optotypes in the first couple of test images. Except for their contrast or sharpness, the first and second optotypes 81o, 82o are identical. They are Snellen letters, and comprise a "Z", a "C" and an "H".

Except from optotypes contrast/sharpness, the first central image 81c is identical to the second central image 82c. Their background is homogeneous, white and luminous.

Regarding now the additional central images 81c', 82c', the second central image 82c comprises at least one additional second optotype 82o' that is sharp and well contrasted (same sharpness and contrast as the first optotypes 81o). And the first additional central image 81c' comprises only one or several additional first optotypes 81o' that have a contrast or sharpness level smaller than a contrast or sharpness level of the at least one additional second optotype 82o'. Except for their contrast or sharpness, the additional first and second optotypes 81o', 82o' are identical: they have the same shape, size, position and orientation within the corresponding test image 81, 82. They are Snellen letters, and comprise an "S", a "Z" and a "D".

Except from optotypes contrast/sharpness, the additional first central image 81c' is identical to the additional second central image 82c'. Their background is homogeneous, white and luminous, like for the first and second central images 81c, 82c.

The first peripheral image 81p of this couple of test images has a uniform dark-grey background, and comprises several abstract crescent-shaped geometrical FIGS. 83, 84, in lighter shades of grey. The second peripheral image 82p is identical to the first peripheral image.

The first transition element 81t of this couple of test images is completely similar to the one 21t of the first couple of test images: it takes the form of a blurred, gradual border delineating the first central image 81c. The additional first central image 81c' is delineated also by such a blurred, gradual border, just as the second central image 82c and the additional second central image 82c'.

In a variant of this fifth couple of test images, the first additional central image 81c', and the second central image 82c could be deprived of optotypes.

Alternatives to the Couples of Test Images Represented in the Figures

Different alternatives have already been described, when presenting the five couples of test images represented in the figures, in particular when presenting the first couple of test images (FIG. 2).

Still, several other alternative couple of test images are possible, according to the invention.

First, any feature of one of the five couples described above can be applied to another of these couples of test images.

For instance, central images having a double Green/Red background for a duochrome test could be employed in the first couple of test images, instead of central images having a one-piece white background.

And, in the fourth couple of test images (FIG. 7), the border of the central background could be blurred (like in FIG. 2), in addition to matching the outline of the image of a part of an object represented in the peripheral image.

And, in the test images of FIG. 8, the peripheral background could be replaced by the peripheral background 25p of FIG. 2, for instance (or conversely).

Besides, in the second, third or fourth couple of test images (FIGS. 5, 6 and 7), the second central image could comprise second optotypes, identical to the first optotypes of the couple of test images considered, except that these second optotypes would have a lower contrast or sharpness, just like the second optotypes of the first couple of test images.

In the second, third, fourth or fifth couple of test images, the first and second peripheral images could be very similar to each other, while not completely identical, as described above for the first couple of test images.

In another alternative, the optotypes could be of the "vanishing" type (such optotypes can be obtained, for instance, by a spatial frequency filtering of standard black-over-white optotypes, in order to remove components having a low spatial frequency). In such a case, the central background would be uniformly gray, instead of being uniformly white.

Besides, in each couple of test images described above, instead of being identical, the first and second peripheral images could be such that, when the first and second test images are superimposed to each other (with their respective frames coinciding with each other), some elements of the first peripheral image are slightly side-shifted with respect to the corresponding elements of the second peripheral image, to enable a stereoscopic 3-D rendering of the scene represented. More precisely, in such a case, the first peripheral image would represent an actual scene, object, or abstract figure as it would be seen from the position of the first eye 2 of the subject, while the second peripheral image would represent to the same scene, object or abstract figure, as it would be seen from the position of the second eye 3 of the subject.

Employing such stereoscopic test images is a very efficient way to get rid of the suppression phenomenon described in the preamble. Indeed, with such test images, the subject has a very strong tendency to try to perceive the scene in a 3-dimentional manner, and thus takes into account both the left and right visual pathway in the fusion process (thus eliminating the "suppression phenomenon"), to obtain this 3-dimensional rendering. When such stereoscopic images are employed, the way to compute their level of similarity has to be adapted, to take into account their 3-dimentional nature.

According to another optional characteristic of these couples of test images, designed for a binocular test of the subject's vision, each of the first and second test images has a feature that depends on a level of ocular dominance of the subject 4.

This feature may be, for instance, the ratio between the area of the first peripheral image and the area of the first central image, this ratio being all the higher as the level of ocular dominance of the subject is high. This enables to strengthen the balancing and stabilizing effect due to the peripheral images, all the more than the ocular dominance of the subject is strong.

In other embodiments not represented in the figures, the first central image has a central background, for instance an homogeneous one, the first peripheral image has a peripheral background, for instance an homogeneous one having a color or shade different from the central background, and the transition element between the first central image and the first peripheral image comprises texture elements, like parchment stains, these texture elements forming together a random or a periodic lattice superimposed to the central background, and superimposed also to the peripheral background.

Such a lattice of texture elements is characterized by different features: the shape, orientation and size of the texture elements (or, in other words, of the patterns of the lattice), their density, and an average distance between adjacent elements of texture. In this last embodiment, at least one of these texture characteristics, associated to the texture elements, is the same in the first peripheral image and in the first central image, or varies gradually from the first peripheral image to the first central image.

Binocular Refraction Methods

Each of the binocular refraction methods described below comprises a preliminary step S0, during which initial values of the first and second refraction corrections are determined. These initial values are not very significantly different from optimal values for which the eyes of the subject would be optimally corrected, that is to say for which the subject has obtained his maximal visual acuity or 10/10 or higher.

These initial values of the first and second refraction corrections may be such that both the first 2 and the second eye 3 of the subject has a visual acuity of 7/10, or more.

In each of these refraction methods, these initial values play the role of starting points. From these starting points, finer values of the first and second refraction corrections are determined, in subsequent steps.

In the preliminary step S0, the initial values of the first and second refraction corrections may be determined by the control unit 8 by acquiring data relative to the refraction errors of the first and second eyes 2, 3 of the subject. These data could be:

a former refraction prescription concerning the subject 4, this prescription being, for instance, inputted by means of a user interface of the instrument 1, loaded from a remote server, read into an electronic health card of the subject 5, or determined from ophthalmic lenses usually worn by the subject 5;

preliminary values of refraction errors of the first and second eyes 2, 3 of the subject, obtained by executing an objective refraction protocol (such as an eccentric photorefraction protocol, or a protocol involving a characterization of a wave front reflected by the retina of the eye considered), prior to the subjective binocular refraction methods described here.

In each of these methods, after the preliminary step S0, a spherical refraction test is carried on for each eye (possibly simultaneously), to determine a value of the equivalent sphere M appropriate to correct the spherical refraction error of the eye considered. Here, the spherical refraction test comprises a fogging and then defogging process. The spherical refraction test is carried on in steps S1 and S1', in step S1", or in step S1''', depending on the method considered (see FIGS. 9, 11 and 13).

After this spherical refraction test, each of these methods comprises an astigmatism test, for determining astigmatism features of each of the eyes 2, 3 of the subject, such as values of the J0 and J45 parameters that are appropriate to correct this eye astigmatism. This test is carried on in steps S2 and S2', in step S2", or in step S2''', depending on the method considered.

And then, each of these methods comprises, for each eye of the subject, a refining test, to refine or to confirm the value of the equivalent sphere M determined previously that may be a duochrome test or a test using optotype of different acuity level. These refining tests correspond to steps S3 and S3', to step S3", or to step S3''', depending on the method considered.

In each of the refraction methods described here, the spherical refraction test comprises at least the following (sub-) steps:

a) providing the first eye 2 with a first refraction correction by means of the first optical unit 5, and providing the second eye 3 with a second refraction correction by means of the second optical unit 6;

b) providing the first eye 2 and the second eye 3 of the subject with the first test image 21, 51, 61, 71, 81 and with the second test image 22, 52, 62, 72, 82 respectively, by means of the image display system 7; and c) varying the first refraction correction provided by the first optical unit 5, depending on at least one indication provided by the subject regarding a sharpness with which the subject perceives the first optotypes 21*o*, 51*o*, 61*o*, 71*o*, 81*o*.

This set of steps, which is generally executed several times successively, enables to adjust the equivalent sphere M of the first refraction correction, so that the first refraction correction gets gradually closer to a refraction correction that optimally corrects the refraction errors of the first eye 2 of the subject.

Of course, a similar set of steps can be executed for the second eye 3 of the subject, to adjust the equivalent sphere M of the second refraction correction, so that it gets gradually closer to a refraction correction that optimally corrects the refraction errors of the second eye 3.

The astigmatism test, or the refining (duochrome) test, could also comprise such a set of steps.

As already explained, providing a first and a second test images as those described above, to the first and second eye of the subject respectively, improves the accuracy of these binocular refraction methods, and enables a faster determination of an appropriate refraction prescription.

Figure 9:
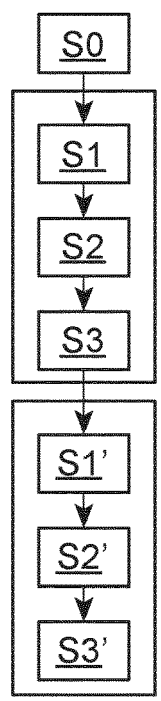
FIGS. 9 and 10 represent schematically some steps of a first binocular refraction method carried on by means of the binocular refraction instrument of FIG. 1.
Figure 11:
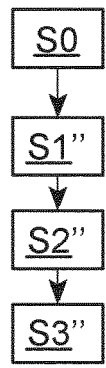
FIGS. 11 and 12 represent schematically some steps of a second binocular refraction method carried on by means of the binocular refraction instrument of FIG. 1.

The first, second and third refraction methods, whose main features have been presented above, are now described in more detail with reference to FIGS. 9, 11 and 13.

First Refraction Method

In the first refraction method, after the preliminary step S0:

the spherical refraction test, the astigmatism test, and then the duochrome test are executed for the first eye 2 of the subject, in steps S1, S2 and S3 respectively, and, subsequently, the spherical refraction test, the astigmatism test, and then the refining (duochrome) test are executed for the second eye 3 of the subject, in steps S1', S2' and S3' respectively.

As already mentioned (in the section relative to the binocular test images), in this first refraction method, the eyes 2, 3 of the subject 4 are provided only one at a time with a test image (such as the first test image 21) in which one or more sharp and well contrasted optotype can be perceived.

So, to determine the refraction correction that is optimal for the first eye 2 of the subject, the first eye 2 and the second eye 3 of the subject could be provided:

with the first test image 21 and with the second test image 22 of FIG. 2 respectively, in step S1;

with the first test image 51, and with the second test image 52 of FIG. 5 respectively, in step S2; and with the first test image 71, and with the second test image 72 of FIG. 7 respectively, in step S3, for the final duochrome test.

Then, to determine the refraction correction that is optimal for the second eye 3 of the subject (in steps S1', S2', S3'), the first and second test images are substituted one to the other, to provide the second eye with test images comprising sharp and well contrasted optotypes. In the case of 3D stereoscopic peripheral images, only the central parts of the first and second test images are substituted one to the other, or replaced respectively by an amended first central part and an amended second central part, that differs in sharp/contrast respectively to initial first and second central parts, to provide the second eye with test images comprising sharp and well contrasted optotypes.

So, in steps S1', the first eye 2 and the second eye 3 of the subject could, for instance, be provided with the second test image 22, and with the first test image 22 of FIG. 2 respectively.

And in step S2', the first eye 2 and the second eye 3 of the subject could be provided with the second test image 52, and with the first test image 52 of FIG. 5 respectively. While in step S3', the first eye 2 and the second eye 3 of the subject could be provided with the second test image 72, and with the first test image 72 of FIG. 7 respectively.

Figure 10:
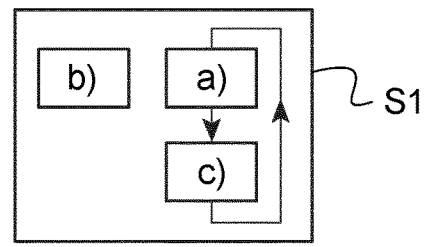

FIG. 10 represents some sub-steps of the spherical refraction test, carried on for the first eye 2 in step S1.

At the beginning of step S1, the control unit 8 controls the first optical unit 5 to set the equivalent sphere M of the first refraction correction to a value slightly higher than the initial value of this equivalent sphere M that was determined in the preliminary step S0, for instance +0.5 or +0.75 diopter higher, to fog the first eye 2.

The equivalent sphere M of the second refraction correction, provided to the second eye 3, can either be set to its initial determined in the preliminary step S0, or be set to a higher value to fog the second eye 3 (which is the fellow eye, during step S1). At this stage, fogging or not the second eye 3 is not essential, as this eye will anyhow be provided with a test image that does not comprise optotypes that can be sharply perceived.

The first and second refraction corrections, thus adjusted, are provided to the subject during the first execution of step a) (FIG. 10).

Meanwhile, step b) is executed: the first and second test images 21, 22 of the first couple of test images, for instance, are provided to the first and second eyes 2, 3 of the subject respectively.

Then, the subject is asked to provide an indication regarding the sharpness with which he/she perceives the optotypes present in the global image he perceives, which corresponds to the sharpness with which he/she perceives the first optotypes 21o. This indication can be provided in a non-direct way, by asking the subject to identify the optotypes (the letters) he/she sees, to test whether the subject sees them sharply (successful identification of the optotypes) or not (failure of the optotypes identification).

Then, depending on this indication, the value of the equivalent sphere M of the first refraction correction is modified, in step c). For instance, if it turned out that the subject didn't perceive sharply the first optotypes, the value of this equivalent sphere is slightly reduced, for instance by subtracting 0.25 or 0.1 diopter to this value.

Then, steps a), b) and c) are executed again, until the subject is able to properly identify small optotypes, having a size corresponding to a visual acuity of 10/10 at least.

Second Refraction Method

The second refraction method is quite similar to the first one, but, in this second refraction method, the first and second refraction corrections are adjusted alternatively, with several alternations between a test and adjustment of the first refraction correction, and a test and adjustment of the second refraction correction.

Steps S1 and S1' are somehow merged together to form step S1".

At the beginning of step S1", both the first eye 2 and the second eye 3 are slightly fogged, just like the first eye 2 at the beginning of step S1.

Then, the equivalent sphere M of the first refraction correction is tested and adjusted by executing one time the steps a), b) and c) described above, like in step S1).

Figure 12:
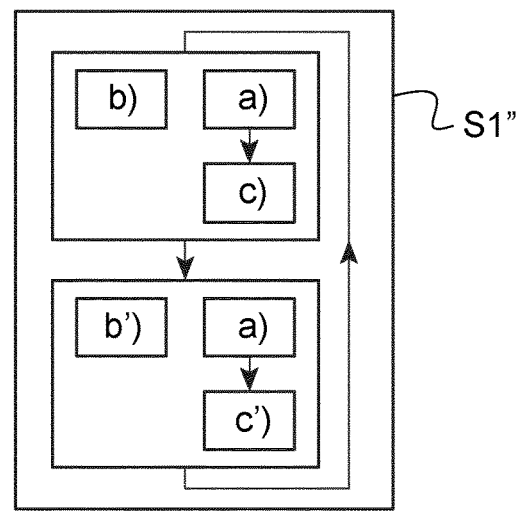

Then, steps a), b'), and then c') are executed (FIG. 12).

In step b'), the image display system 7 provides the first eye 2 with the second test image 22 of the first couple of test images, and provides the second eye 3 with the first test image 21 of this couple of test images.

And in step c'), the second refraction correction is varied on the basis of at least one indication provided by the subject regarding a sharpness with which the subject perceives the first optotypes 21o, which, in this situation, depends on the second refraction corrections, not on the first one (as the first test image is provided to the second eye of the subject). And then, the group of steps comprising steps a), b), c), a), b'), c') is repeated, until the subject is able to properly identify small optotypes, having a size corresponding to a visual acuity of 10/10 at least, should these optotypes be provided to the first eye, or to the second eye of the subject.

Similarly, in step S2", the astigmatism features of the first refraction correction, and those of the second refraction correction are adjusted alternatively, by small steps, with several alternations between an adjustment of the first refraction correction, and an adjustment of the second refraction correction.

In a variant of this second method, the alternations between an adjustment of the first refraction correction, and an adjustment of the second refraction correction could be less frequent than in the case of FIG. 12. For instance, the complete fogging/defogging process could be carried on for the first eye, and then for the second eye. And then, the astigmatism features of the first eye, and then of the second eye could be determined. In such a variant, the refraction method would comprise, in this order: step S0, step S1, step S1', step S2, step S2', step S3 and then step S3'.

Third Refraction Method

As already mentioned, in the third binocular refraction method, both the first test image 81 and the second test image 82, provided to the first eye and to the second eye of the subject, comprise at least one sharp and well contrasted optotype 81o, 82o' (but displayed in different parts 81c, 82c' of the subject's field of view). So, the first and second refraction corrections can be assessed simultaneously by the subject.

In this third method, at the beginning of step S1''', the control unit 8 controls the first optical unit 5 to set the equivalent sphere M of the first refraction correction to a value slightly higher than the initial value of this equivalent sphere determined in the preliminary step S0 (for instance +0.5 or +0.75 diopter higher), to fog the first eye. And, similarly, the control unit 8 controls the second optical unit 6 to set the equivalent sphere M of the second refraction correction o a value slightly higher that its initial value, determined in the preliminary step S0 (for instance +0.5 or +0.75 diopter higher), to fog also the second eye.

Figure 14:
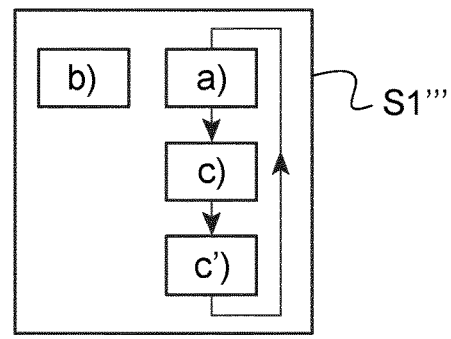

The first and second refraction corrections, thus adjusted, are provided to the subject during the first execution of step a) (FIG. 14).

Meanwhile, step b) is executed: the first and second test images 81, 82 of the fifth couple of test images (FIG. 8) are provided to the first and second eyes 2, 3 of the subject respectively.

Then, the subject is asked to provide an indication regarding the sharpness with which he/she perceives the optotypes present in the let part of the global image he perceives, which correspond to the sharpness with which he/she perceives the first optotypes 81o (see FIG. 8). This indication can be provided in a non-direct way, by asking the subject to identify the optotypes (the letters) he/she sees, to test whether the subject sees them sharply (successful optotypes identification) or not (identification failure).

Then, depending on this indication, the value of the equivalent sphere M of the first refraction correction is modified, in step c) (as explained about step S1).

Then, the subject is asked to provide an indication regarding the sharpness with which he/she perceives the optotypes present in the right part of the global image he perceives, which correspond to the sharpness with which he/she perceives the additional second optotypes 82o'. This indication can be provided in a non-direct way, as explained above.

Then, depending on this indication, the value of the equivalent sphere M of the second refraction correction is modified, in step c').

Then, the set of steps comprising steps a), b) c) and c') is executed again, possibly several times, until the subject is able to properly identify small optotypes, having a size corresponding to a visual acuity of 10/10 at least, both in the left part and in the right part of the image he perceives.

Step S2''' is similar to step S1''', except that it starts with the first and second refraction corrections obtained at the end of step S1''', and that the optotypes employed are not letters, but optotypes appropriate to test astigmatism features (like those of FIG. 5).

Step S3''' starts with the first and second refraction corrections obtained at the end of step S2''', and is carried on with central images appropriate for a refining (duochrome) test, like in FIG. 7.

Several alternatives to these methods are possible, according to the invention. For instance, each of these method could comprise just one of the tests mentioned above, namely the spherical refraction test, the astigmatism test and the refining (duochrome) test, instead of all these tests.

The refraction measurement method and images used in the instrument of the present disclosure may use interactive elements or steps. The whole examination process may lead to build a narrative story. A keyboard or pad may be used to input the answers of the subject or to enable the subject to go back to previous scenes if he/she wishes to. An indicator may be used to display graphically the degree of advancement of the refraction examination process. Transition videos could be incorporated at various times of the refraction examination process between two consecutive tests to display graphically the degree of advancement of the refraction examination process while improving the comfort of the subject, helping to maintain her/his attention and adding a pleasant context of the examination process. Accordingly, such video could display a boat advancing on the sea, with the horizon line being more and more visible as the video progresses. This illustrations are accompanied by the sound of waves. Each video lasts 5 seconds. The sound of wave and the videos showing a boat moving on the see were chosen because they consist in natural elements. They aim to relax the subjects, reduce their stress and re-engage their attention. A progress bar is also visible on the videos, to indicate to subjects the current stage of the examination. This allows to add an element of progression to the exam in order to improve the comfort of the subjects, help them maintain their attention and add a pleasant joyful context. In addition, knowing which level of the exam is pending, and the number of remaining steps, gives them an idea of the time remaining, which facilitates concentration. Explanations on the test and/or a playful, nice story telling explaining the test and focusing on some objects that will be shown during the test (treasure hunt like test) may be given at the beginning of the tests in order to get attention, cooperation and understanding of tests (questions/answers) from the subject and above all to make sure that the subject is not stressed during the visual examination.

The invention claimed is:

1. A binocular refraction instrument comprising:
 a first optical unit with adjustable refractive power features;
 a second optical unit with adjustable refractive power features;
 an image display system configured to provide a first test image to a first eye of a subject and, at the same time, configured to provide a second test image to a second eye of the subject, the first test image being seen by the first eye of the subject through the first optical unit and the second test image being seen by the second eye of the subject through the second optical unit; and
 control circuitry programmed to control the first and second optical units and the image display system in order to:
  a) provide the first eye with a first refraction correction by the first optical unit, and apply to the second eye a second refraction correction by the second optical unit;
  b) provide the first eye and the second eye of the subject with the first test image and with the second test image respectively by the image display system, the first and second test images being such that:
   the first test image comprises a first central image surrounded by a first peripheral image, the first central image comprising at least one first optotype;

the second test image comprises a second central image surrounded by a second peripheral image;

each of said first and second peripheral images is non-uniform, and a level of similarity between the first and second peripheral images is higher than a given threshold;

the second central image is different from the first central image, the second central image being deprived of optotype or comprising only one or several second optotypes that have a contrast or sharpness level smaller than a contrast or sharpness level of said at least one first optotype; and c) varying said first refraction correction by way of the first optical unit depending on at least one indication provided by the subject regarding a sharpness with which the subject perceives said at least one first optotype, the control circuitry is further programmed so that the first test image includes a transition element which, for at least one image characteristic:

provides a continuous transition from said first central image to said first peripheral image, a quantity representative of said at least one image characteristic, has the same value in the first central image and in the first peripheral image, or varies gradually from the first central image to the first peripheral image, so that the first central image appears to be integrated into the first peripheral image.

2. The binocular refraction instrument according to claim 1, wherein the control circuitry is programmed so that:

the first central image comprises a first central background over which the at least one first optotype is superimposed, and the transition element comprises a border delineating said first central background, and said at least one image characteristic comprises at least one of the following: an image luminosity, a color feature, and an image element outer shape.

3. The binocular refraction instrument according to claim 2, wherein the control circuitry is programmed so that the first peripheral image has a first peripheral background and so that:

said at least one image characteristic comprises said image luminosity, said image luminosity having a peripheral luminosity value in the first peripheral background and having a central luminosity value in the first central background, said image luminosity varying gradually and monotonically from said peripheral luminosity value to said central luminosity value along a line traversing said border, or so that said at least one image characteristic comprises said color feature, said color feature having a peripheral color value in the first peripheral background and having a central color value in the first central background, said color feature varying gradually and monotonically from said central color value to said peripheral color value along a line traversing said border.

4. The binocular refraction instrument according to claim 2, wherein the control circuitry is programmed so that the first peripheral image comprises an image of an object and in which said at least one image characteristic comprises said image element outer shape, a part of the object represented in the first peripheral image having the same outer shape as the first central background, an outline of the image of said part of said object coinciding with the border of the first central background.

5. The binocular refraction instrument according to claim 1, wherein the control circuitry is programmed so that the first central image comprises a first balancing element and the second central image comprises a second balancing element, the first balancing element having a shape, a size and/or a position within the first test image that are substantially identical to a shape, a size and/or a position within the second test image of the second balancing element.

6. The binocular refraction instrument according to claim 5, wherein:

said first balancing element is said at least one first optotype, and said second balancing element is one of said one or several second optotypes, which has a shape substantially identical to a shape of said at least one first optotype.

7. The binocular refraction instrument according to claim 1, wherein the second central image comprises said one or several second optotypes, and in which the contrast or sharpness level of said one or several second optotypes is small enough to cause an acuity decrease by a factor of 2 at least for said second eye, compared to optypes perfectly sharp and having a contrast of 100 percent.

8. The binocular refraction instrument according to claim 1, in which the second central image comprises said one or several second optotypes, the contrast of the said one or several second optotypes being comprised between 1 percent and 20 percent, and in which the contrast of said at least one first optotype is higher than 50 percent.

9. The binocular refraction instrument according to claim 1, in which at least one of said first and second test images has a feature that depends on a level of ocular dominance of the subject.

10. The binocular refraction instrument according to claim 1, wherein:

the first test image comprises an additional first central image, distinct from the first central image and surrounded by said first peripheral image, the second test image comprises an additional second central image, distinct from the second central image (82c), surrounded by said second peripheral image and that comprises at least one additional second optotype, and the first additional central image is different from the second additional central image, the first additional central image being deprived of optotype or comprising only one or several additional first optotypes that have a contrast or sharpness level smaller than a contrast or sharpness level of said at least one additional second optotype.

11. The binocular refraction instrument according to claim 1, wherein the control circuitry is programmed to control the first and second optical units and the image display system in order to execute several times successively the ensemble that comprises: a), b), c), and then a), b'), c'), wherein:

in b'), the image display system provides the first eye with an amended first central image, and provides the second eye with an amended second central image, amended first and second central images differ at least in sharp and/or contrast respectively to initial first and second central images, the amended first central image being preferably the initial second central image, and the amended second central image being preferably the initial first central image; and in c'), the second refraction correction is varied on the basis of at least one indication provided by the subject regarding a sharpness with which the subject perceives said at least one first optotype.

12. A non-transitory computer readable medium having stored thereon a set of images comprising a first test image and a second test image, to be provided to a first eye of a subject and to a second eye of the subject respectively, by a binocular refraction instrument, for determining at least one refraction feature of the first eye of the subject in a binocular manner, including a first optical unit with adjustable refractive power features, a second optical unit with adjustable refractive power features, an image display system configured to provide a first test image to a first eye of a subject and, at the same time, configured to provide a second test image to a second eye of the subject, the first test image being seen by the first eye of the subject through the first optical unit and the second test image being seen by the second eye of the subject through the second optical unit, and control circuitry programmed to control the first and second optical units and the image display system in order to: a) provide the first eye with a first refraction correction by the first optical unit, and apply to the second eye a second refraction correction by the second optical unit, b) provide the first eye and the second eye of the subject with the first test image and with the second test image respectively by the image display system, the first and second test images being such that: the first test image comprises a first central image surrounded by a first peripheral image, the first central image comprising at least one first optotype, the second test image comprises a second central image surrounded by a second peripheral image, each of said first and second peripheral images is non-uniform, and a level of similarity between the first and second peripheral images is higher than a given threshold, the second central image is different from the first central image, the second central image being deprived of optotype or comprising only one or several second optotypes that have a contrast or sharpness level smaller than a contrast or sharpness level of said at least one first optotype, and c) varying said first refraction correction by way of the first optical unit depending on at least one indication provided by the subject regarding a sharpness with which the subject perceives said at least one first optotype, wherein:

the first test image comprises a first central image surrounded by a first peripheral image, the first central image comprising at least one first optotype;

the second test image comprises a second central image surrounded by a second peripheral image;

each of said first and second peripheral images is non-uniform, and a level of similarity between the first and second peripheral images is higher than a given threshold;

the second central image is different from the first central image, the second central image being deprived of optotype or comprising only one or several second optotypes that have a contrast or sharpness level smaller than a contrast or sharpness level of said at least one first optotype; and the first test image includes a transition element which, for at least one image characteristic, provides a continuous transition from said first central image to said first peripheral image, and wherein the control circuitry is further programmed so that the first test image includes a transition element which, for at least one image characteristic:

provides a continuous transition from said first central image to said first peripheral image, a quantity representative of said at least one image characteristic, has the same value in the first central image and in the first peripheral image, or varies gradually from the first central image to the first peripheral image, so that the first central image appears to be integrated into the first peripheral image.

13. A binocular refraction method, implemented by a binocular refraction instrument including a first optical unit with adjustable refractive power features, a second optical unit with adjustable refractive power features, and an image display system for providing a first test image to a first eye of a subject and, at the same time, for providing a second test image to a second eye of the subject, the first test image being seen by the first eye of the subject through the first optical unit and the second test image being seen by the second eye of the subject through the second optical unit, the method comprising:

a) providing the first eye of the subject with a first refraction correction by the first optical unit, and providing the second eye of the subject with a second refraction correction by the second optical unit;

b) providing the first eye and the second eye with the first test image and with the second test image respectively by the image display system, wherein:

the first test image comprises a first central image surrounded by a first peripheral image, the first central image comprising at least one first optotype, the second test image comprises a second central image surrounded by a second peripheral image, wherein the first test image includes a transition element which, for at least one image characteristic:

provides a continuous transition from said first central image to said first peripheral image, a quantity representative of said at least one image characteristic, has the same value in the first central image and in the first peripheral image, or varies gradually from the first central image to the first peripheral image, so that the first central image appears to be integrated into the first peripheral image;

each of said first and second peripheral images is non-uniform, and a level of similarity between the first and second peripheral images is higher than a given threshold, and the second central image is different from the first central image, the second central image being deprived of optotype or comprising only one or several second optotypes that have a contrast or sharpness level smaller than a contrast or sharpness level of said at least one first optotype; and c) varying said first refraction correction by way of the first optical unit depending on at least one indication provided by the subject regarding a sharpness with which the subject perceives said at least one first optotype.

14. A non-transitory computer readable medium having stored thereon a program comprising instructions which, when the program is executed by control circuitry of a binocular refraction instrument, cause the binocular refraction instrument to carry out the method of claim 13.

* * * * *